United States Patent
Zillmer et al.

(10) Patent No.: US 7,391,031 B1
(45) Date of Patent: Jun. 24, 2008

(54) DETECTION OF PEROXIDES AND SUPEROXIDES WITH FAST NEUTRONS

(75) Inventors: Andrew J. Zillmer, Woodland Hills, CA (US); Gregory A. Johnson, Camarillo, CA (US)

(73) Assignee: Pratt & Whitney Rocketdyne, Inc., Canoga Park, CA (US)

( * ) Notice: Subject to any disclaimer, the term of this patent is extended or adjusted under 35 U.S.C. 154(b) by 0 days.

(21) Appl. No.: 11/641,583

(22) Filed: Dec. 19, 2006

(51) Int. Cl.
*G01N 23/09* (2006.01)
(52) U.S. Cl. .................................. 250/390.04
(58) Field of Classification Search ............. 250/390.04
See application file for complete search history.

(56) References Cited

U.S. PATENT DOCUMENTS

| | | | |
|---|---|---|---|
| 3,124,679 A | 3/1964 | Tittman et al. | |
| 3,146,349 A | 8/1964 | Jordan | |
| 3,832,545 A | 8/1974 | Bartko | |
| 4,864,142 A | 9/1989 | Gomberg | |
| 4,882,121 A | 11/1989 | Grenier | |
| 5,076,993 A | 12/1991 | Sawa et al. | |
| 5,078,952 A | 1/1992 | Gozani et al. | |
| 5,098,640 A | 3/1992 | Gozani et al. | |
| 5,293,414 A | 3/1994 | Ettinger et al. | |
| 5,373,538 A | 12/1994 | Grenier et al. | |
| 5,557,108 A | 9/1996 | Tumer | |
| 5,982,838 A | 11/1999 | Vourvopoulos | |
| 6,393,085 B1 | 5/2002 | Heller et al. | |
| 6,438,189 B1 | 8/2002 | Vourvopoulos | |
| 6,563,898 B1 | 5/2003 | Vourvopoulos et al. | |
| 6,928,131 B2 | 8/2005 | Olshansky et al. | |

*Primary Examiner*—Constantine Hannaher
*Assistant Examiner*—Marcus H Taningco
(74) *Attorney, Agent, or Firm*—Kinney & Lange, P.A.

(57) ABSTRACT

A system for detecting a compound in a sample includes a neutron source, at least one gamma ray detector positioned proximate the sample, and a signal processor. The neutron source directs a neutron beam toward the sample. The gamma ray detector collects gamma rays emitted from the sample and the signal processor determines the compounds in the sample based on the gamma rays collected by the gamma ray detector. The compound is selected from the group consisting of peroxides and superoxides.

20 Claims, 2 Drawing Sheets

DETECTION OF PEROXIDES AND SUPEROXIDES WITH FAST NEUTRONS

BACKGROUND OF THE INVENTION

The present invention generally relates to the field of detecting compounds in a sample. In particular, the invention relates to detecting peroxides and superoxides in a sample.

Although peroxides and superoxides by themselves can be inert chemicals, they can pose a large threat when mixed with other chemicals. The combination of peroxides and superoxides with other chemicals, such as organics, can be used to make explosives. For example, a mixture of hydrogen peroxide and acetone is capable of producing an unstable, explosive reaction. Because organics, such as acetone, are present in numerous household products, it is more efficient to monitor the presence of peroxides and superoxides in sealed containers. By detecting and prohibiting large amounts of oxidizers in sensitive areas, the threat of mixing two chemicals to form an explosive fuel can be greatly reduced.

A method currently being used to detect explosives is to use a small neutron source to detect the presence of nitrogen. Nitrogen in a sample can indicate nitrates, which is a common oxidizer in explosives. As the neutrons hit atoms in the sample, they react with the atoms and produce gamma rays. The energy, number, and intensity of gamma rays produced from the sample are measured to determine whether the sample contains specified amounts of nitrogen. If necessary, the sample can then be pulled and examined for explosive potential. However, this technique of detecting nitrogen is not capable of detecting peroxides or superoxides. The ability to quickly and accurately detect oxidizers being housed within sealed containers can help prevent explosive chemicals from being carried onto vehicles such as airplanes, trains, buses, etc.

BRIEF SUMMARY OF THE INVENTION

A system for detecting a compound in a sample includes a neutron source, at least one gamma ray detector positioned proximate the sample, and a signal processor. The neutron source directs a neutron beam toward the sample. The gamma ray detector collects gamma rays emitted from the sample and the signal processor determines the compounds in the sample based on the gamma rays collected by the gamma ray detector. The compound is selected from the group consisting of peroxides and superoxides.

DETAILED DESCRIPTION

Figure 1:
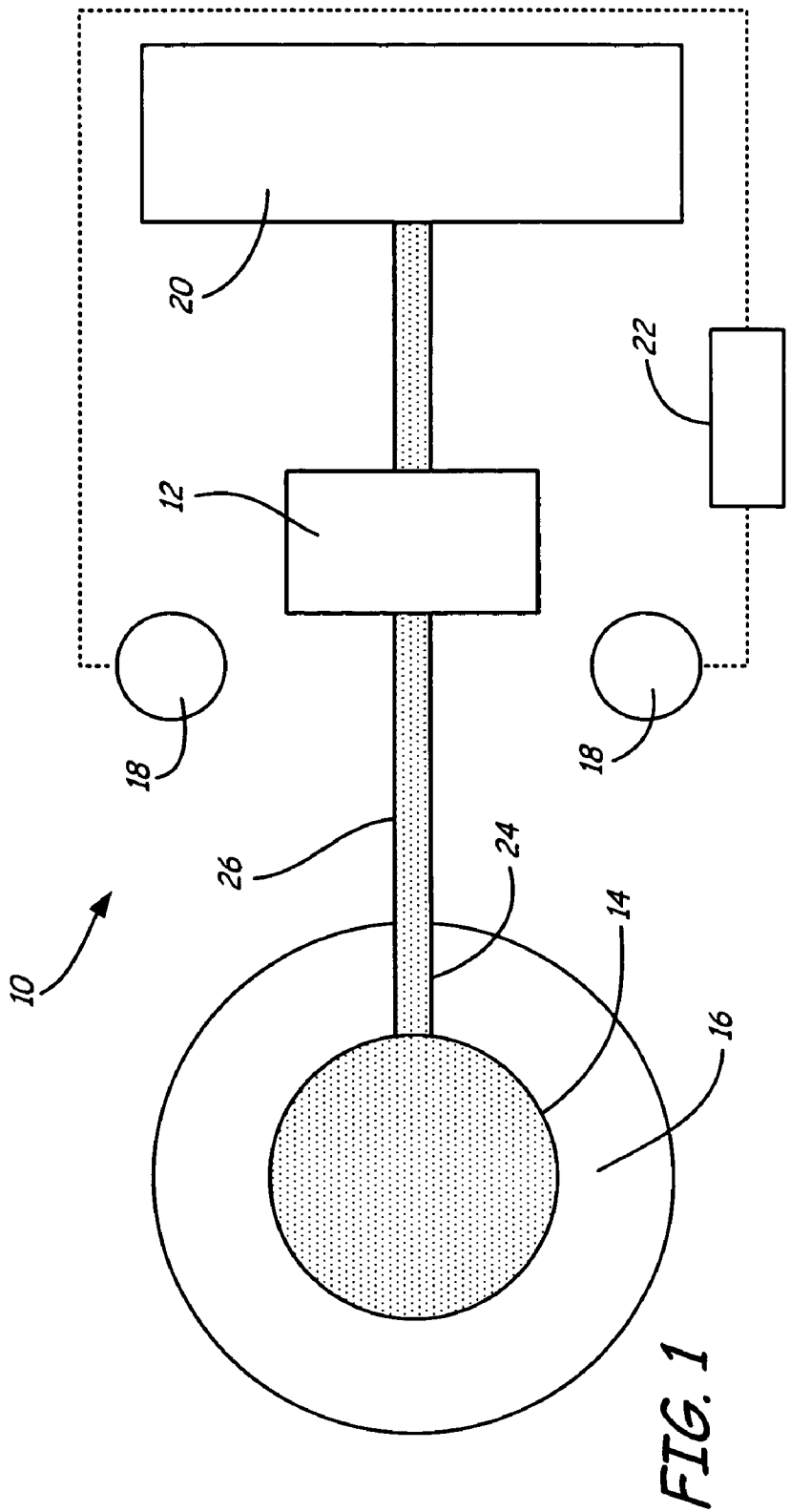
FIG. 1 is a schematic view of a detection system used to detect peroxides and superoxides in a sample.

FIG. 1 shows a schematic view of detection system 10 used to detect peroxides and superoxides in sample 12. Detection system 10 generally includes neutron source 14, shield 16, gamma ray detectors 18, beam dump 20, and signal processor 22. Detection system 10 allows for quick and accurate detection of hazardous chemicals in sample 12, which may be, for example, a closed container. In particular, because peroxides and superoxides can be used in combination with other chemical compounds to form explosives, detecting peroxides and superoxides can significantly help prevent the threat of explosions. Examples of peroxides that are potentially dangerous include, but are not limited to: hydrogen peroxide and acetone peroxide. Examples of superoxides that are potentially dangerous include, but are not limited to: sodium superoxide, potassium superoxide, cesium superoxide, and rubidium superoxide. Although FIG. 1 is discussed in terms of detecting peroxides and superoxides, detection system 10 may be used to detect any number of compounds or elements, including nitrogen atoms.

Neutron source 14 is positioned upstream of sample 12 and directs fast neutrons toward sample 12. Shield 16 surrounds neutron source 14 to help minimize radiation close to personnel and to prevent damage to objects in close proximity to neutron source 14. Shield 16 has an opening 24 that aligns a beam of neutrons 26 from neutron source 14 with sample 12. Neutron beam 26 is sent from neutron source 14 toward sample 12 at energies sufficient to produce gamma rays from hydrogen atoms and oxygen atoms, the primary constituents in peroxides and superoxides. In one embodiment, neutron source 14 directs neutron beam 26 at energies greater than at least 6 Million Electron Volts (MeV). As neutron beam 24 strikes sample 12, the neutrons react with the atoms in sample 12 and produce gamma rays at discrete energies based on the atoms present in sample 12. Neutron source 14 may include, but is not limited to: a compact neutron source, a fusion neutron source, or a nuclear reactor with a fast neutron spectrum.

Gamma ray detectors 18 are positioned proximate sample 12 and detect the gamma rays released when neutron beam 26 strikes sample 12. Gamma ray detectors 18 have energy resolutions that allow gamma ray detectors 18 to measure the energy, number, and intensity of the gamma rays produced by sample 12 based on the specific energies of the neutrons in neutron beam 24. The energy, number, and intensity of gamma rays are collected by gamma ray detectors 18 and are used to determine the concentrations of hydrogen and oxygen in sample 12. The ratio of gamma ray energies can then be measured and compared to determine if sample 12 has a higher concentration of peroxide or superoxide than an amount predetermined as potentially dangerous. In one embodiment, gamma ray detectors 18 may include, but are not limited to: high purity germanium, cadmium zinc telluride, and thallium-doped sodium iodide.

The number and intensity of the gamma rays produced by sample 12 are then sent to signal processor 22 and recorded. Signal processor 22 analyzes the amounts, intensities, energies, and ratios of gamma rays to determine the elements that make up sample 12 and provide an output to a user. Because gamma ray detectors 18 are capable of measuring the energy, number, and intensity of atoms present in sample 12, signal processor 22 can distinguish the presence of peroxides and superoxides from the presence of other, less harmful compounds. This is because each element produces gamma rays at particular energies and gamma ray detectors 18 are capable of recording the particular energies and intensities of the gamma rays produced to be analyzed by signal processor 22. For example, the presence of peroxide, which is composed of two hydrogen atoms and two oxygen atoms, can be distinguished from the presence of water, which is composed of two hydrogen atoms and one oxygen atom. Because water has a different chemical composition than peroxide, the presence of water will give a different signal than peroxide. Peroxides will have a higher ratio of oxygen gamma rays to hydrogen gamma rays than water.

When neutron beam 24 reaches sample 12, some of the neutrons will not strike sample 12. The neutrons in neutron beam 24 that pass through sample 12 continue on to beam dump 20, which acts as a shield and collects the neutrons to ensure that they do not unintentionally strike personnel or other objects proximate detection system 10.

Figure 2:
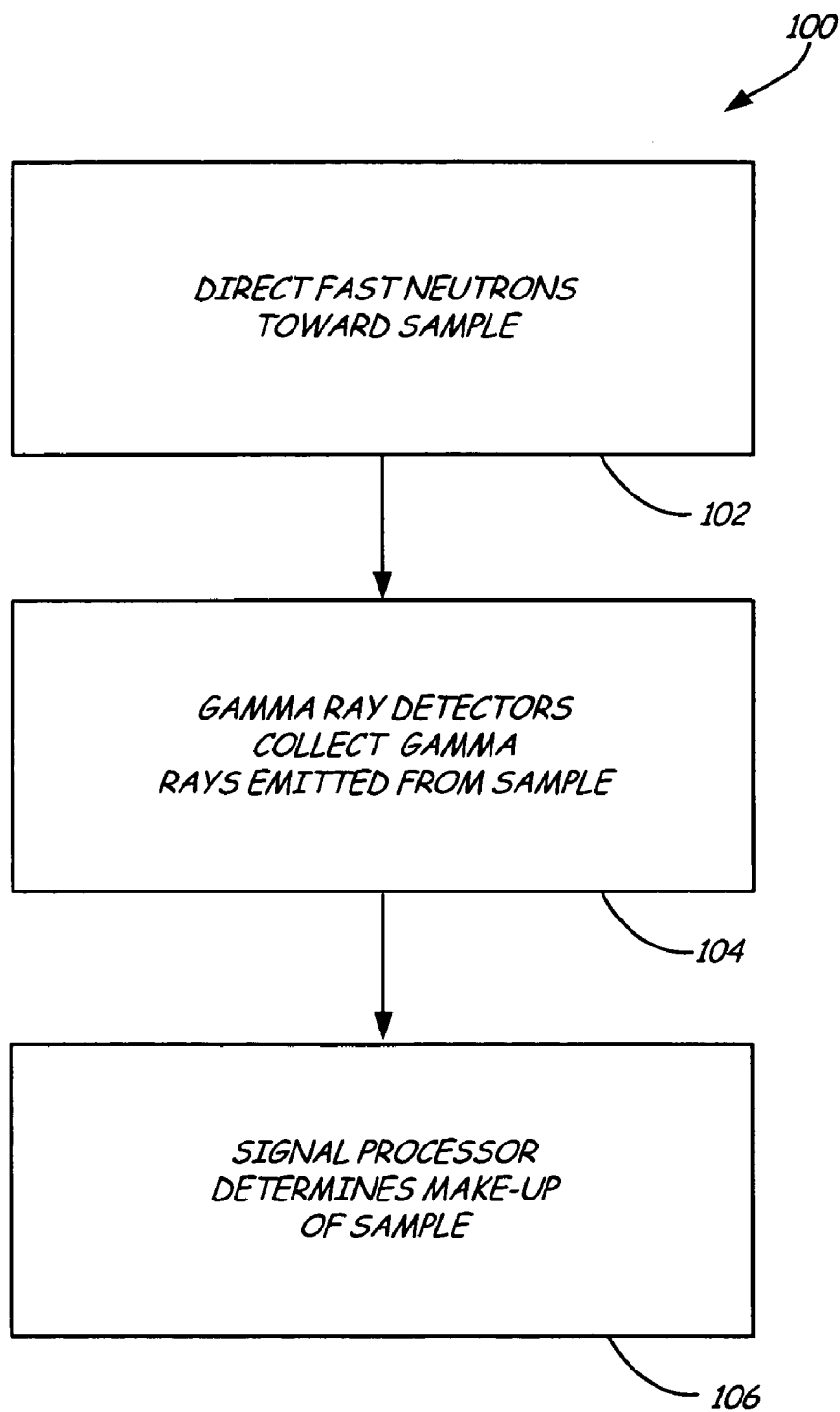
FIG. 2 is a diagram of a method of detecting peroxides and superoxides in a sample.

FIG. 2 shows a diagram of a method 100 of detecting peroxides and superoxides in sample 12. When a sample is to be examined for peroxides or superoxides, neutron source 14 emits neutron beam 24 through opening 22 of shield 16 toward sample 12, Box 102. As neutron beam 24 strikes sample 12, the neutrons react with the atoms present in sample 12 and gamma rays are released. A plurality of gamma ray detectors 18 are positioned proximate sample 12 and detect the gamma rays produced from sample 12, Box 104. In one embodiment, gamma ray detectors 18 measure the type, number, and intensity of gamma rays released from sample 12. As depicted in Box 106, the information collected from gamma ray detectors 18 is then sent to signal processor 26, which uses the information to determine the concentration of atoms present in sample 12. Signal processor 26 may then provide an output detailing the make up of sample 12 to a user. Any neutrons from neutron beam 24 that do not strike sample 12 are subsequently collected in beam dump 20.

The detection system detects potentially dangerous compounds, such as peroxides and superoxides, which may be housed in a sealed container. Fast neutrons are emitted from a neutron source toward the sample to be examined at energies high enough to release gamma rays from hydrogen atoms and oxygen atoms. A shield with an opening aligned with the sample is positioned around the neutron source to protect personnel from the neutron beam. As the neutron beam strikes the sample, gamma rays are released and detected by a plurality of gamma ray detectors positioned proximate the sample. The gamma ray detectors detect the energy, number, and intensity of the gamma rays being released from the sample. The energy, number, and intensity of gamma rays can be used to determine the amount of hydrogen and oxygen atoms present in the sample. Any remaining neutrons that do not strike the sample are collected in a beam dump positioned downstream of the sample. The quick and accurate detection of peroxides and superoxides in samples may reduce the potential threat of explosives on vehicles.

Although the present invention has been described with reference to preferred embodiments, workers skilled in the art will recognize that changes may be made in form and detail without departing from the spirit and scope of the invention.

The invention claimed is:

1. A system for detecting an oxidizer in a container, the system comprising:
   a neutron source for directing a neutron beam toward the container;
   at least one gamma ray detector positioned proximate the container for collecting gamma rays emitted from the oxidizer; and
   a signal processor for determining the oxidizer in the container from the gamma rays collected by the gamma ray detector;
   wherein the oxidizer to be detected is selected from the group consisting of superoxides.

2. The system of claim 1, wherein the oxidizer to be detected is further selected from the group consisting of metal superoxides.

3. The system of claim 1, and further comprising a shield surrounding at least a portion of the neutron source and a beam dump positioned downstream of the sample.

4. The system of claim 1, and further comprising a plurality of gamma ray detectors.

5. The system of claim 1, wherein the neutron beam is directed toward the sample at an energy of at least 6 Million Electron Volts.

6. The system of claim 1, wherein the gamma ray detector is a high purity germanium crystal detector.

7. The system of claim 1, wherein the gamma ray detector is a thallium-doped sodium iodide detector.

8. A system for detecting a superoxide oxidizer in a closed container, the system comprising:
   a neutron source for directing a neutron beam toward the closed container at an energy of at least 6 Million Electron Volts;
   at least one gamma ray detector positioned proximate the closed container for detecting gamma rays produced by the superoxide oxidizer; and
   a signal processor for analyzing the gamma rays detected by the gamma ray detector.

9. The system of claim 8, wherein the superoxide oxidizer is an inorganic chemical that forms an explosive fuel when mixed with an organic chemical.

10. The system of claim 8, and further comprising a shield for directing the neutron beam from the neutron source in one direction and a beam dump positioned to intercept the neutron beam downstream of the sample.

11. The system of claim 8, and further comprising a plurality of gamma ray detectors.

12. The system of claim 8, wherein the superoxide oxidizer is a metal superoxide.

13. The system of claim 12, wherein the metal superoxide is selected from the group consisting of sodium superoxide, potassium superoxide, cesium superoxide and rubidium superoxide.

14. The system of claim 8, wherein the gamma ray detector is a high purity germanium crystal detector.

15. The system of claim 8, wherein the gamma ray detector is a thallium-doped sodium iodide detector.

16. A method of detecting inorganic superoxides in a container, the method comprising:
   passing fast neutrons through the container;
   detecting gamma rays released from the inorganic superoxides in the container; and
   analyzing the gamma rays released from the inorganic superoxides in the container;
   wherein the fast neutrons are passed through the source at energies of at least 6 Million Electron Volts.

17. The method of claim 16, wherein detecting gamma rays comprises detecting the number of gamma rays released from the sample.

18. The method of claim 16, wherein detecting gamma rays comprises detecting the intensity of gamma rays released from the sample.

19. The method of claim 16, wherein the inorganic superoxides to be detected in the sample are metal superoxides.

20. The method of claim 16, wherein the inorganic superoxides to be detected in the sample form explosive fuels when mixed with organic chemicals.

* * * * *